United States Patent [19]
Woo

[11] Patent Number: 5,639,474
[45] Date of Patent: Jun. 17, 1997

[54] CYCLOSPORIN SOFT CAPSULE COMPOSITION

[75] Inventor: Jong Soo Woo, Kyunggi-do, Rep. of Korea

[73] Assignee: Hanmi Pharm. Ind., Ltd., Kyunggi-do, Rep. of Korea

[21] Appl. No.: 427,465

[22] Filed: Apr. 24, 1995

Related U.S. Application Data

[63] Continuation-in-part of Ser. No. 177,495, Jan. 5, 1994, abandoned.

[30] Foreign Application Priority Data

Jul. 1, 1993 [KR] Rep. of Korea ............... 93-12291

[51] Int. Cl.$^6$ ................ A61K 9/10; A61K 9/48; A61K 38/13
[52] U.S. Cl. ............ 424/452; 424/451; 424/455; 424/456; 514/784; 514/785; 514/786; 514/937; 514/962; 514/970; 514/975; 514/885; 514/11
[58] Field of Search ............ 424/451, 452, 424/455, 456; 514/784, 785, 786, 937, 962, 970, 975, 885, 11

[56] References Cited

U.S. PATENT DOCUMENTS 5,589,455 12/1996 Woo ............................ 514/11

*Primary Examiner*—Thurman K. Page
*Assistant Examiner*—James M. Spear
*Attorney, Agent, or Firm*—Lowe, Price, LeBlanc & Becker

[57] ABSTRACT

The present invention relates to a microemulsion concentrate containing cyclosporin as an active ingredient, dimethylisosorbide as a cosurfactant, oil and a surfactant which is suitable for the formulation of a soft capsule for oral administration, said cyclosporin, dimethyl isosorbide, oil and surfactant being present in the ratio of 1:1-5:1-5:2-10, and preferably in the ratio of 1:2-4:2-5:2-4:7, by weight. Since dimethylisosorbide has substantially no membrane permeation property, the soft capsule preparation according to the present invention is outstandingly stable in comparison with the soft capsules containing ethanol, propylene glycol, transcutol, glycofurol, etc., as a cosurfactant in the prior art, and further provides an advantage in that the pharmaceutical effect, appearance and composition content of the soft capsule according to the present invention are not changed.

10 Claims, 4 Drawing Sheets

CYCLOSPORIN SOFT CAPSULE COMPOSITION

CROSS-REFERENCE TO RELATED APPLICATION

This application is a continuation in part of application Ser. No. 08/177,495 filed Jan. 5, 1994 now abandoned.

BACKGROUND OF THE INVENTION

1. Field of the invention

The present invention relates to a soft capsule composition containing a stable microemulsion concentrate suitable for the preparation of cyclosporin-containing soft capsules. More particularly, the present invention relates to a microemulsion concentrate containing cyclosporin as an active ingredient, dimethylisosorbide as a co-surfactant, an oil component and a surfactant, which is suitable for formulation into soft capsules and to a soft capsule composition containing said microemulsion concentrate.

2. Background art

Cyclosporin is a specific macromolecular (molecular weight 1202.64) cyclic peptide compound consisting of 11 amino acids, which has useful pharmacological activities, particularly immunosuppressive activity and anti-inflammatory activity. Therefore, cyclosporin has been used for suppression of immunological responses native to the living body, which are caused by tissue and organ transplantation, for example, transplantation of the heart, lung, liver, kidney, pancreas, bone marrow, skin and cornea, and particularly the transplantation of foreign tissues and organs. In addition, cyclosporin is useful for the suppression of autoimmune diseases and inflammatory diseases such as arthritis, etc.

Cyclosporin is highly lipophilic and hydrophobic with a solubility in water at 25° C. being 16 to 23 mg of cyclosporin per liter of water. The bioavailability of cyclosporin is also extremely low due to its low water-solubility. On the other hand, cyclosporin is well dissolved in an organic solvent such as methanol, ethanol, acetone, ether, chloroform and the like, due to its high lipophilic property.

As with other conventional drugs which are sparingly soluble in water, cyclosporin is very difficult to formulate into a preparation for oral administration due to its low water solubility and bioavailability. Further, since the bioavailability of cyclosporin may be greately influenced by the condition of each individual patient, it is very difficult to provide an effective therapeutic effect.

Moreover, it is very important to provide a uniform dosage amount and appropriate bioavailability since counterbalancing the efficacy of cyclosporin are its considerable toxic side effects such as nephrotoxicity, hepatotoxicity, among others. Accordingly, numerous studies have been extensively and widely conducted to find a preparation suitable for the effective oral administration of cyclosporin.

The prior art preparations suitable for oral administration of sparingly water-soluble cyclosporin are usually formulated in the form of a microemulsion. In preparing the liquid microemulsion formulation, cyclosporin should be combined with a surfactant, an oil and a cosurfactant. One method using this combination is taught in U.S. Pat. No. 4,388,307 which issued on Jun. 14, 1983. This patent discloses a liquid formulation of cyclosporin using ethanol as a cosurfactant. Thus, cyclosporin is combined with a carrier consisting of ethanol as a cosurfactant, a vegetable oil and a transesterification product of a natural vegetable oil triglyceride and a polyalkylene glycol as a surfactant to form the liquid formulation. However, the resulting liquid formulation is administered as an aqueous dilution making it very difficult to properly formulate the preparation to provide a uniform dosage for oral administration.

In order to alleviate the requirement of diluting the cyclosporin liquid composition in water prior to oral administration, a liquid composition in the form of a microemulsion concentrate has been formulated into a soft capsule preparation, which is presently commercially available as SANDIMMUN® (trademark). In this preparation the cyclosporin soft capsule contains a large amount of ethanol as a cosurfactant due to the solubility requirements of cyclosporin. However, since ethanol, which has a low boiling point, permeates the gelatin membrane of the capsule to volatilize even at normal temperature, the constitutional ratio of the contents in soft capsules varies during storage. The reduced ethanol content results in a significant difference in the bioavailability of cyclosporin and making the problem worse, the cyclosporin crystallizes when the soft capsules are stored at low temperature.

In an effort to prevent the volatilization of ethanol from the soft capsule preparations during storage and distribution, the soft capsule preparations are wrapped in a packing material, such as an aluminum film foam package. However, such specific packaging does not completely maintain the uniform composition of the wrapped capsule. It has been demonstrated through experiments that although the cyclosporin soft capsule is wrapped up in aluminum film foam package, the ethanol content is lowered to 7.9% from the initial level of 10.8% after a period of one week. This results in a great difference in bioavailability and may contribute to the increase of its price.

To solve the above-mentioned disadvantages which accompany the use of ethanol as a cosurfactant, a method using a non-ethanol component as a cosurfactant has been proposed. Korean Laid-open Patent Publication No. 90-4348 (Apr. 12, 1990) discloses a pharmaceutical composition in the form of a microemulsion concentrate containing a non-ethanol component. The non-ethanol components include pharmaceutically acceptable $C_{1-5}$ alkyl or tetrahydrofurfuryl di- or partial-ether of low molecular mono- or poly-oxy-alkanediol, for example, diethyleneglycol monoethyl ether [e.g. Transcutol] or tetrahydrofurfuryl alcohol polyethylene glycol ether [e.g. Glycofurol], or 1,2-propyleneglycol as a cosurfactant. However, the above non-ethanol cosurfactants are glycols which contain the -OH group in their structures. It has now been identified that the OH group-containing glycol creates problems in the formulation of soft capsules because its strong absorption property is sufficient to absorb the moisture from the atmosphere and also because it is highly permeable to the gelatin film of the soft capsule.

Thus, the present inventors have studied numerous additives, including various solvents, in an effort to find a cosurfactant capable of providing a microemulsion concentrate suitable for the formulation of cyclosporin into a soft capsule preparation. As a result, a certain pharmaceutically acceptable solvent, dimethyli- sosorbide [Trade name: ARLASOVE® DMI, available from ICI Speciality Chemicals] has been found as a suitable solvent for this purpose to complete the present invention.

Therefore, it is an object of the present invention to provide a microemulsion concentrate containing dimethylisosorbide as a cosurfactant, which is suitable for formulation into soft capsules for oral administration.

It is a further object of the present invention to provide a microemulsion concentrate suitable for formulation into soft capsules, which contains cyclosporin as an active ingredient, dimethylisosorbide as a cosurfactant, an oil component and a surfactant.

Further, it is another object of the present invention to provide a soft gelatin capsule composition according to the present invention which is highly storage stable such that there is little variation of the composition over time.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention and the drawings, in addition to the scope of the invention defined by the claims.

BRIEF DESCRIPTION OF THE DRAWINGS

For a thorough understanding of the nature and objects of the invention, reference should be had to the following detailed description taken in connection with the accompanying drawings in which.

DISCLOSURE OF INVENTION

Figure 1:
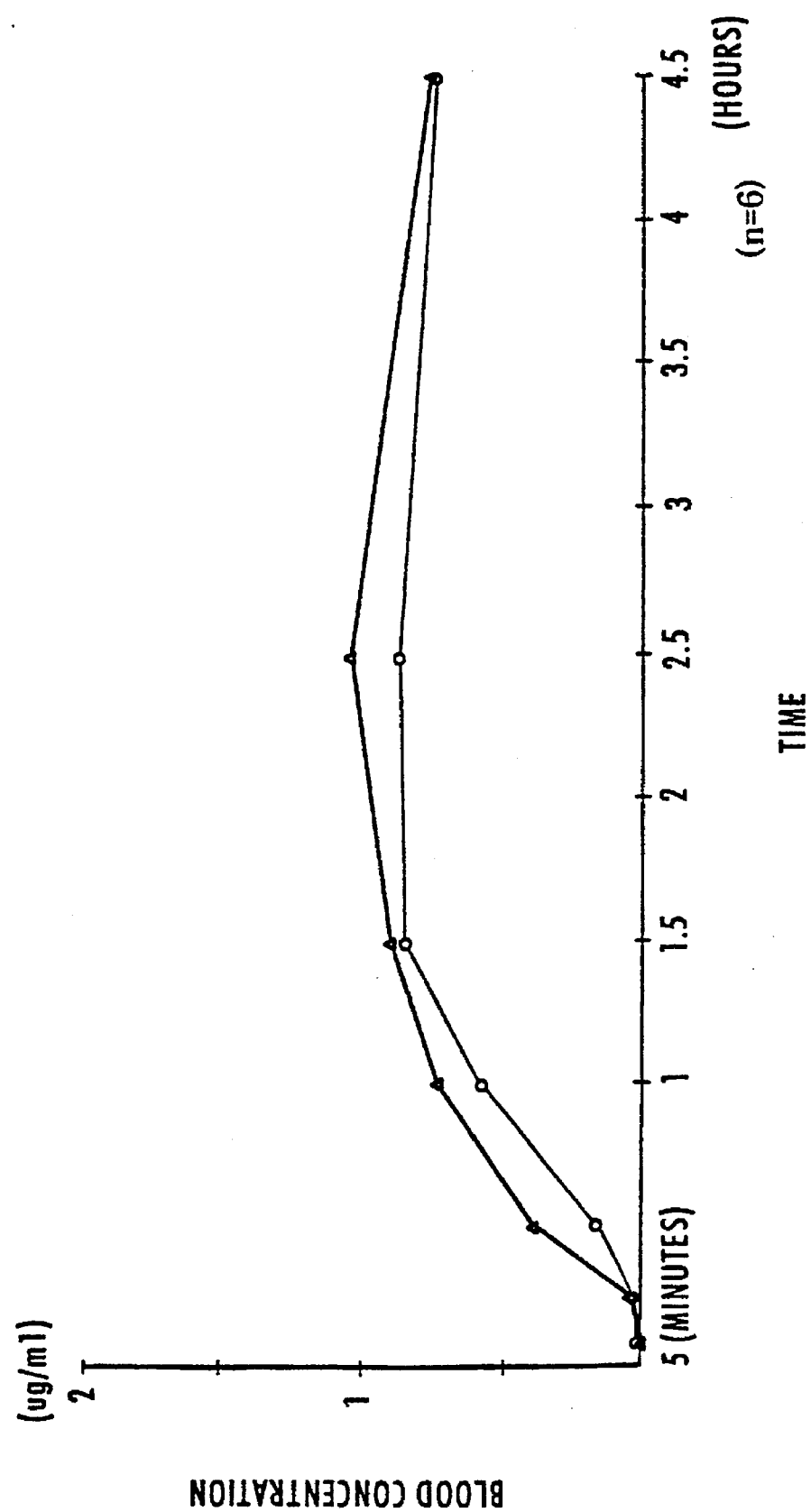
FIG. 1 is a graph showing the change in blood concentration over time after cyclosporin microemulsion concentrate containing dimethylisosorbide as a cosurfactant according to Example 1 (△—△) and cyclosporin microemulsion concentrate containing ethanol as a cosurfactant (○—○) are orally administered.

In one aspect, the present invention relates to a microemulsion concentrate comprising cyclosporin as an active ingredient, dimethylisosorbide as a cosurfactant, an oil component and a surfactant which is suitable for the formulation of soft capsules for oral administration.

Cyclosporin, the first essential component, is the pharmaceutically active ingredient in the microemulsion concentrate according to the present invention. Cyclosporin is a cyclic peptide compound having useful immunosuppressive activity and antiinflammatory activity as described above and known in the art. Although cyclosporin A, B, C, D, G and the like can be used as the cyclosporin component in the present invention, cyclosporin A is most preferred since its clinical effectiveness and pharmacological properties are well established in the art.

The dimethylisosorbide cosurfactant, which is the second essential component in the microemulsion concentrate according to the present invention, is a compound represented by the following structural formula. Dimethylisosorbide has been used as a skin permeation stimulator in topical pharmaceutical compositions. The chemical name of dimethylisosorbide is 1,4:3,6-dianhydro-2,5-dimethyl-D-glucitol.

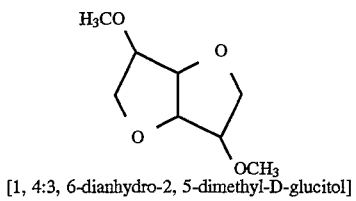

[1, 4:3, 6-dianhydro-2, 5-dimethyl-D-glucitol]

Since dimethylisosorbide has a high boiling point, 234° C., it does not volatilize even at high temperature such as the temperature necessary for manufacturing soft capsules. In addition, dimethylisosorbide does not contain any hydroxy groups, —OH, and therefore, its hygroscopic property is very low and it does not permeate the gelatin membrane of the soft capsule. Most importantly, cyclosporin dissolves well in dimethylisosorbide which contributes to the formulation of a suitable microemulsion as defined above.

Accordingly, the use of dimethylisosorbide as a cosurfactant in the microemulsion concentrate of the present invention provides certain advantages. That is, when the microemulsion concentrate is formulated into a soft capsule, a change in the composition of the concentrate does not appear during storage and the contents of the components contained therein are substantially uniformly maintained so that the uniformity of the composition content can be assured over a greater time period than ethanol based compositions.

In the microemulsion concentrate of the present invention, dimethylisosorbide is used in the ratio of 1 to 5 parts by weight and preferably 2 to 4 parts by weight, per 1 part by weight of cyclosporin.

The third component used in the microemulsion concentrate according to the present invention is an oil(s). The oil component suitable for use in the present invention includes any animal or vegetable oils which are pharmaceutically acceptable. Thus, neutral animal oils and vegetable oils, for example, castor oil or corn oil, particularly animal oil rich in unsaturated fatty acids having an iodine value of 180 to 200, for example, refined fish oil and vegetable oil having the hydroxyl value of 150, for example, castor oil, are preferably used. Among such oils, the most preferred oil is refined fish oil. Refined fish oil is ideally fit for the absorption of cyclosporin since it contains EPA (eicosapentaenoic acid), a highly unsaturated fatty acid, and DHA (docosahexaenoic acid) in the amount of 18%, or more, and 12%, or more, respectively, having a total unsaturated fatty acid content of 30%, or more, which allows for the absorption of cyclosporin.

The oil component according to the present invention may include only a single oil selected from the above-mentioned oils or a mixture selected from the above-mentioned oils.

When a mixture of two or more oil components is used, it is preferred that at least one animal oil and at least one vegetable oil be present in said mixture.

In addition, if required, in the oil component the appropriate amount of saturated fatty acids, for example, caprilic acid/capric triglyceride [Trademark: MIGLYOL® 812; Dynamit Nobel Chemikalien] can be included in order to control the absorption of cyclosporin. When such saturated fatty acid is added to the oil component, it can modulate the absorption pattern of cyclosporin to reduce the occurrence of typical side effects involved in cyclosporin preparations.

The fourth essential component used in the microemulsion concentrate according to the present invention is a surfactant. The suitable surfactants for use in the present invention include any of pharmaceutically acceptable surfactant capable of stably emulsifying the lipophilic portion of the composition comprising the cyclosporin-containing oil component and the hydrophilic part comprising the cosurfactant in water to form a stable microemulsion. The most preferred surfactants according to the present invention include polyoxyethylene glycolated natural or hydrogenated vegetable oils, transesterification reaction products of natural vegetable oil triglyceride and polyalkylene polyol, sorbitan fatty acid esters, polyoxyethylene-sorbitan fatty acid esters, polyoxyethylene alcohols, etc., such as the reaction products of castor oil and ethylene oxide, which are commercially available under the trade mark CREMOPHOR® (BASF), the esterification reaction products of natural vegetable oil and polyethylene glycol, which are commercially available under the trade mark LABRAFIL® (Etablissement Gattefosse), the sorbitan fatty acid esters which are commercially available under the trade mark SPAN® (Lippo Chemicals) and the polyoxyethylene alcohols which are commercially available under the trade mark BRIJ® (BASF). Among these surfactants, LABRAFIL® M 1944 CS (apricot kernel oil PEG-6 ester) having the HLB Value of 14.0 to 15.0 is the most preferred. The surfactant may include any one of the abovementioned surfactants alone or, preferably, in a combination of mentioned surfactants alone or, preferably, in a combination of one or more surfactants selected from the above surfactants.

In the microemulsion concentrate according to the present invention, four essential components are present preferably in the ratio of cyclosporin:cosurfactant:oil component:surfactant=1:1-5:1-5:2-10, and more preferably in the ratio of cyclosporin: cosurfactant:oil component:surfactant=1:2-4:2-5:2-7 by weight. The most preferable microemulsion concentrate according to the present invention consists of cyclosporin A, dimethylisosorbide, LABRAFIL® and refined fish oil in the ratio of 1:4:3:2.7 by weight. In addition to this composition, the composition illustrated in the following examples can be mentioned as the further preferable compositions according to the present invention.

For oral administration, the microemulsion concentrate having the above-mentioned composition, according to the present invention, can be formulated into the form of a soft capsule. In formulating the soft capsule, the capsule preparation can further contain, if necessary, pharmaceutically acceptable adjuvants, excipients and additives which are conventionally utilized in the preparation of soft capsules, in addition to the above microemulsion concentrate. Such additives include, for example, lecithin, viscosity regulator, perfume (e.g. peppermint oil, etc.), antioxidant (e.g. tocopherol, etc.), preservative (e.g. parabens, etc.), coloring agent, glyerin, sorbitol, gelatine, etc.

The soft capsule preparation according to the present invention can be prepared according to conventional methods for the preparation of soft capsules. For example, cyclosporin is first dissolved in dimethylisosorbide while gently warming at the temperature of approximately 60° C. The oil component and the surfactant are then added to the resulting mixture and the whole mixture is uniformly mixed. The resulting microemulsion concentrate is then introduced into a machine for preparing soft capsules, with or without the above-mentioned pharmaceutically acceptable additives conventionally utilized in preparation of soft capsules, to prepare the desired suitable cyclosporin soft capsule. The soft capsule composition thus prepared according to the present invention exhibits a blood level of cyclosporin comparable to that of the prior art ethanol-containing soft capsule preparation when they are administered by mouth, i.e. orally. Further the soft capsule composition according to the present invention is stably maintained without any change over a prolonged storage period. Accordingly, it is readily apparent that the present invention provides a significant improvement in the field of preparation of the cyclosporin soft capsules.

The present invention will be more specifically illustrated by the following examples. However, it should be understood that the present invention is not limited by these examples in any manner.

EXAMPLE 1

2.5 g of cyclosporin A was added to 4.5 g of dimethylisosorbide (ARLASOLVE® DMI). The mixture was warmed to about 60° C. with stirring to dissore cyclosporin. To the resulting solution were added 7.5 g of LABRAFILRM® M 1944CS (apricot kernel oil PEG-6 ester) and 11.5 g of refined fish oil and the mixture was sufficiently stirred until the homogeneous microemulsion concentrate was formed. The microemulsion concentrate thus obtained was introduced into a machine for preparation of soft capsules, which is adjusted so that 0.26g of the microemulsion concentrate is injected into one soft capsule, to prepare the soft gelatin capsules containing the cyclosporin microemulsion concentrate within gelatin sheets.

EXAMPLE 2

The soft gelatin capsules having the following compositions were prepared according to the same procedure as Example 1 except that the amount of dimethylisosorbide as a cosurfactant is varied.

| | Component | Content (mg/Cap.) |
|---|---|---|
| 2-A. | Cyclosporin | 25 |
| | Dimethylisosorbide (ARLASOLVE$^R$ DMI) | 25 |
| | LABRAFIL$^R$ M 1944 CS | 75 |
| | Refined fish oil | 115 |
| | Total | 240 mg |
| 2-B. | Cyclosporin | 25 |
| | Dimethylisosorbide (ARLASOLVE$^R$ DMI) | 65 |
| | LABRAFIL$^R$ M 1944 CS | 75 |
| | Refined fish oil | 115 |
| | Total | 280 mg |

EXAMPLE 3

The soft gelatin capsules having the following compositions were prepared according to the same procedure as Example 1 except that as the surfactant the mixture of LABRAFIL® and another surfactant is used instead of LABRAFIL® alone.

| Component | Content (mg/Cap.) |
|---|---|
| 3-A. Cyclosporin | 25 |
| Dimethylisosorbide (ARLASOLVE^R DMI) | 45 |
| LABRAFIL^R M 1944 CS | 75 |
| CREMOPHOR^R EL | 5 |
| Refined fish oil | 115 |
| Total | 265 mg |
| 3-B. Cyclosporin | 25 |
| Dimethylisosorbide (ARLASOLVE^R DMI) | 45 |
| LABRAFIL^R M 1944 CS | 75 |
| SPAN^R 20 | 5 |
| Refined fish oil | 115 |
| Total | 265 mg |
| 3-C. Cyclosporin | 25 |
| Dimethylisosorbide (ARLASOLVE^R DMI) | 45 |
| LABRAFIL^R M 1944 CS | 75 |
| BRIJ^R 35 | 5 |
| Refined fish oil | 115 |
| Total | 265 mg |

EXAMPLE 4

The soft gelatin capsules having the following compositions were prepared according to the same procedure as Example 1 except that the oil component and its content are changed.

| Component | Content (mg/Cap.) |
|---|---|
| 4-A. Cyclosporin | 25 |
| Dimethylisosorbide (ARLASOLVE^R DMI) | 45 |
| LABRAFIL^R M 1944 CS | 75 |
| Refined fish oil | 55 |
| Total | 200 mg |
| 4-B. Cyclosporin | 25 |
| Dimethylisosorbide (ARLASOLVE^R DMI) | 45 |
| LABRAFIL^R M 1944 CS | 75 |
| Refined fish oil | 115 |
| Total | 320 mg |
| 4-C. Cyclosporin | 25 |
| Dimethylisosorbide (ARLASOLVE^R DMI) | 45 |
| LABRAFIL^R M 1944 CS | 75 |
| Refined fish oil | 115 |
| Caprilic acid/Capric triglyceride | 40 |
| Total | 300 mg |
| 4-D. Cyclosporin | 25 |
| Dimethylisosorbide (ARLASOLVE^R DMI) | 45 |
| LABRAFIL^R M 1944 CS | 75 |
| Corn oil | 115 |
| Total | 260 mg |
| 4-E. Cyclosporin | 25 |
| Dimethylisosorbide (ARLASOLVE^R DMI) | 45 |
| LABRAFIL^R M 1944 CS | 100 |
| Castor oil | 115 |
| Total | 285 mg |
| 4-F. Cyclosporin | 25 |
| Dimethylisosorbide (ARLASOLVE^R DMI) | 45 |
| LABRAFIL^R M 1944 CS | 80 |
| Refined fish oil | 69 |
| Castor oil | 46 |
| Total | 265 mg |

EXAMPLE 5

The soft gelatin capsule having the following composition was prepared according to the same procedure as Example 1, except that peppermint oil (perfume) and tocopherol (antioxidant) are additionally added to the microemulsion concentrate before it is formulated into the soft capsule.

| Component | Content (mg/Cap.) |
|---|---|
| Cyclosporin | 25 |
| Dimethylisosorbide (ARLASOLVE^R DMI) | 45 |
| LABRAFIL^R M 1944 CS | 75 |
| Refined fish oil | 115 |
| Peppermint oil | 20 |
| Tocopherol | 5 |
| Total | 285 mg |

EXAMPLE 6

The soft gelatin capsule having the following composition was prepared according to the same procedure as Example 1.

| Component | Content (mg/Cap.) |
|---|---|
| Cyclosporin | 25 |
| Dimethylisosorbide (ARLASOLVE^R DMI) | 50 |
| LABRAFIL^R M 1944 CS | 75 |
| Refined fish oil | 115 |
| Castor oil | 3.5 |
| d-α-Tocopherol | 1.5 |
| Total | 270 mg |

EXAMPLE 7

The soft gelatin capsule having the following composition was prepared according to the same procedure as Example 1.

| Component | Content (mg/Cap.) |
|---|---|
| Cyclosporin | 25 |
| Dimethylisosorbide (ARLASOLVE^R DMI) | 100 |
| LABRAFIL^R M 1944 CS | 75 |
| Refined fish oil | 68.5 |
| d-α-Tocopherol | 1.5 |
| Total | 270 mg |

EXAMPLE 8

The membrane permeation property of dimethylisosorbide over the storage period at the room temperature was examined for the soft capsules prepared using dimethylisosorbide (ARLASOLVE® DMI) as a cosurfactant according to the present invention and then compared with the membrane permeation properties of ethanol, propylene glycol, Transcutol (diethylene glycol monoethyl ether) and Glycofurol (tetrahydrofurfuryl alcohol polyethylene glycol ether). The content of the cosurfactant in each soft capsule preparation was analyzed by gas chromatography. The components and their constitutional ratios in the compositions used in this experiment are given in the following Table 1 and the experiment results are given in the following Table 2.

TABLE 1

Composition of the soft capsules used in the test for membrane permeation property

| | Content of each component in capsule | | | | |
|---|---|---|---|---|---|
| | Test | Control preparation (cosurfactant) | | | |
| Component | preparation (dimethyl-isosorbide) | A (ethanol) | B (propylene-glycol) | C (Trans-cutol) | D (Glyco-furol) |
| Cyclosporin | 25 mg (10.8 wt %) | 25 mg (10.8 wt %) | 25 mg (10.8 wt %) | 25 mg (10.8 wt %) | 25 mg (10.8 wt %) |
| Cosurfactant | 25 mg (10.8 wt %) | 25 mg (10.8 wt %) | 46 mg (10.8 wt %) | 46 mg (19.8 wt %) | 46 mg (19.8 wt %) |
| Oil component (Soybean oil) | 105.8 mg (46.0 wt %) | 106.5 mg (46.0 wt %) | 115 mg (49.6 wt %) | 115 mg (49.6 wt %) | 115 mg (49.6 wt %) |
| Surfactant (LABRAFIL® M2125CS) | 74.52 mg (32.4 wt %) | 75 mg (32.4 wt %) | 46 mg (19.8 wt %) | 46 mg (19.8 wt %) | 46 mg (19.8 wt %) |

TABLE 2

Change in the contents of cosurfactants contained in soft capsules over the storage period

| | Change in contents (per capsule) | | | | | |
|---|---|---|---|---|---|---|
| | Initial | Storage period (days) | | | | |
| Cosurfactant | content | 2 | 5 | 12 | 14 | 50 |
| Dimethylisosorbide (Test preparation) | 10.8 | 10.8 | 10.5 | 10.4 | 10.0 | 9.8 |
| Ethanol (Control preparation A) | 10.8 | 7.2 | 3.8 | 2.1 | 1.3 | — |
| Propylene glycol (Control preparation B) | 19.8 | 3.6 | 0.9 | — | — | — |
| Transcutol (Control preparation C) | 19.8 | 7.3 | — | — | 2.7 | — |
| Glycofurol (Control preparation D) | 19.8 | 8.2 | — | — | 3.2 | — |

Note: Conditions of gas chromatography for each cosurfactant

1) Dimethylisosorbide

Column: Ultra 2 (Cross-linked 2% phenylmethyl silicone gun phase, 25 m×0.32 mm, thickness 0.52 μm)
   Column temperature: 230° C. (Isothermal)
   Detector: FID (Temperature: 270° C.)
   Injection temperature: 275° C.
   Carrier gas: He (Partition ratio 80:1)
   Injection volume: 5 μl
   Internal standard: Octyl alcohol 2) Ethanol Column: HP-20M (Carbowax 20M) (25 m×0.32 mm, film thickness 0.3 μm)
   Column temperature: 30° C. (Isothermal)
   Detector: FID (Temperature: 200° C.)
   Injection temperature: 150° C.
   Carrier gas: He (Partition ratio 80:1)
   Injection volume: 5 μl
   Internal standard: Diethyl ether 3) Propylene glycol Column: HP-20M (Carbowax 20M) (25 m×0.32 mm, film thickness 0.3 μm)
   Column temperature: 180° C. (Isothermal)
   Detector: FID (Temperature: 240° C.)
   Injection temperature: 240° C.
   Carrier gas: He (Partition ratio 80:1)
   Injection volume: 5 μl
   Internal standard: Pentadecanoic acid methyl ester 4) Transcutol Column: Ultra 2 (Cross-linked 5% phenylmethyl silicone gun phase, 25 m×0.32 mm, thickness 0.52 μm)
   Column temperature: 230° C. (Isothermal)
   Detector: FID (Temperature: 270° C.)
   Injection temperature: 270° C.
   Carrier gas: He (Partition ratio 80:1)
   Injection volume: 5 μl
   Internal standard: Pentadecanoic acid methyl ester 5) Glycofurol Column: Ultra 2 (Cross-linked 2% phenylmethyl silicone gun phase, 25 m×0.32 mm, thickness 0.52 μm)
   Column temperature: 230° C. (Isothermal)
   Detector: FID (Temperature: 270° C.) p1 Injection temperature: 270° C.
   Carrier gas: He (Partition ratio 80:1)
   Injection volume: 5 μl
   Internal standard: Dimethylisosorbide As can be seen from the results described in the above Table 2, dimethylisosorbide used as a cosurfactant according to the present invention does not change in its content even after 50 days while other cosurfactants used in the prior art were reduced by 50% of the initial content after only 2 days. Accordingly, it can be readily determined that dimethylisosorbide when used as a cosurfactant according to the present invention exhibits substantially no membrane permeation since the amount thereof does not significantly change in the composition and therefore is most suitable for use in the formulation of soft capsule preparations according to the present invention.

EXAMPLE 9

The bioavailability of the microemulsion using dimethylisosorbide as a cosurfactant according to the present invention was compared with the bioavailability of an ethanol-containing preparation according to the prior art to estimate the influence of dimethylisosorbide on the bioavailability of cyclosporin. In this experiment, rabbits were used as the experimental animal. The soft capsules as prepared in Example 1, Example 6 and Example 7 and the commercialized product SANDIMMUN® using ethanol as a cosurfactant were used as the test preparations and the control preparation, respectively. In this experiment, both of the test preparations and the control preparation were administered in an amount of 300 mg as cyclosporin per kg of rabbit. Rabbits were uniformly fed with the conventional rabbit solid feed composition for 4 days or more under the same condition in wire cages. When the oral preparations were administered, rabbits were fasted for 48 hours in a restraint cage made of wood, during which rabbits were allowed to freely take 10% dextrose solution. Levin's tube having a diameter of 5 mm was interposed by the depth of 30 cm through the esophagus after the surface of the Levin's tube was coated with vaseline in order to reduce friction. Each of the test preparations and the control preparation was emulsified with 50 ml of water and then introduced into a syringe which is attached to the Levin's tube. Ear veins of rabbit were dilated using xylene and then blood was taken from each rabbit's ear vein at an interval of 5, 15, 30, 60, 90, 150 and 270 minutes by means of heparin-treated disposable syringe. To 1 ml of blood thus obtained were added 0.5 ml of aqueous saturated sodium chloride solution and 2 ml of ether, and then the mixture was shaken for 5 minutes and centrifuged with 5000 rpm for 10 minutes to separate the supernatant. 1 ml of the supernatant was collected and then developed in an activated silica SEP-PAK® (Waters). The developed SEP-PAK® was washed with 5 ml of n-hexane and eluated with 2 ml of methanol. The eluate was evaporated to dryness in nitrogen gas under reduced pressure. The residue was analyzed by means of HPLC (High Performance Liquid Chromatography) [HPLC condition: Column µ-BONDAPAK® $C_{18}$ (Waters), Mobile phase $CH_3CN$: $MeOH:H_2O=55:15:30$, Detection 210 nm, Flow rate 1.0 ml/min., Column temperature 70° C., Sensitivity 0.01 Aufs, Injection volume 100 µl].

Figure 2:
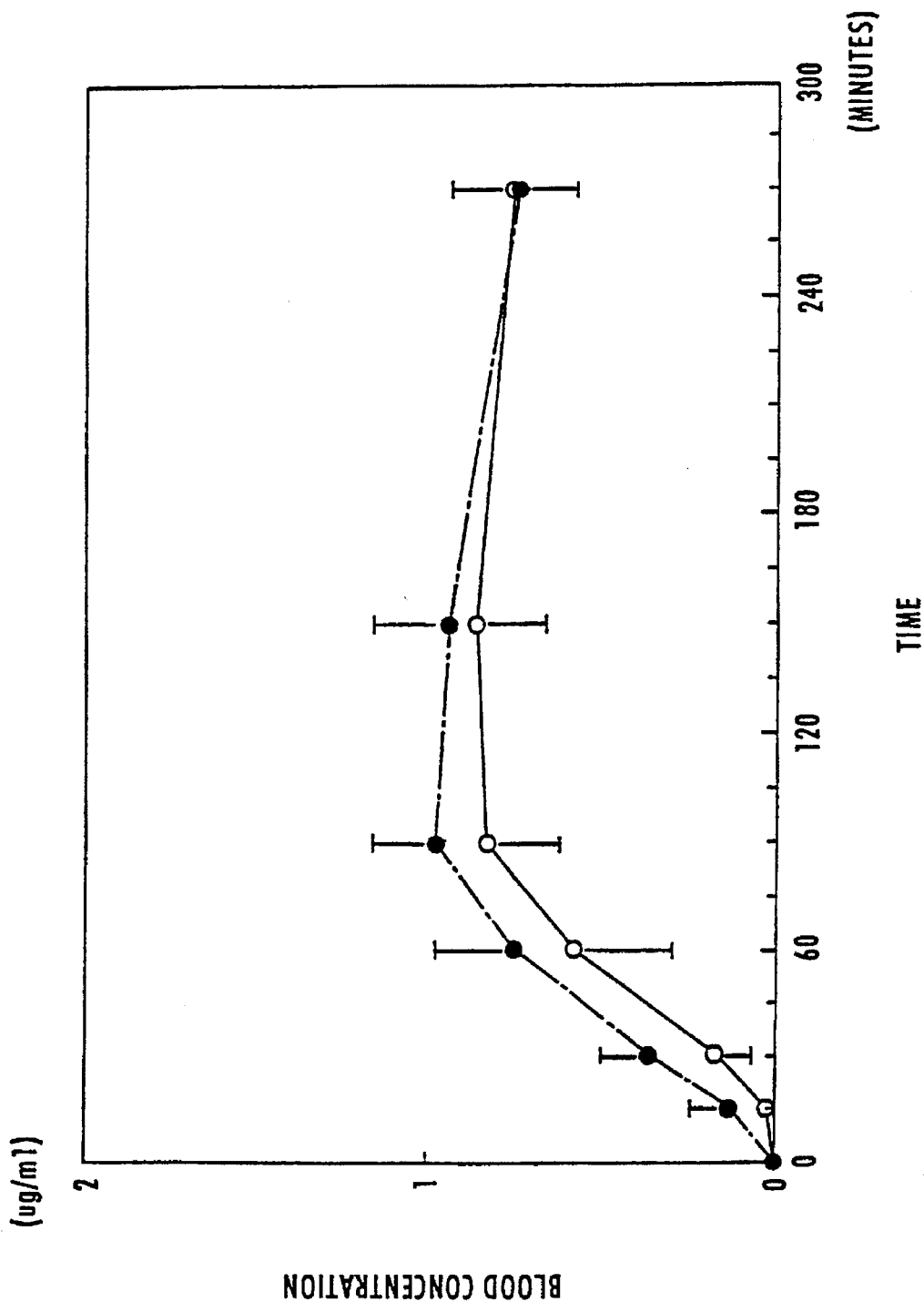
FIG. 2 is a graph showing the change in blood concentration over time after cyclosporin microemulsion concentrate containing dimethylisosorbide as a cosurfactant according to Example 6 (●—●) and cyclosporin emulsion concentrate containing ethanol as a cosurfactant (○—○) (SANDIMMUN®) are orally administered to rabbit.
Figure 3:
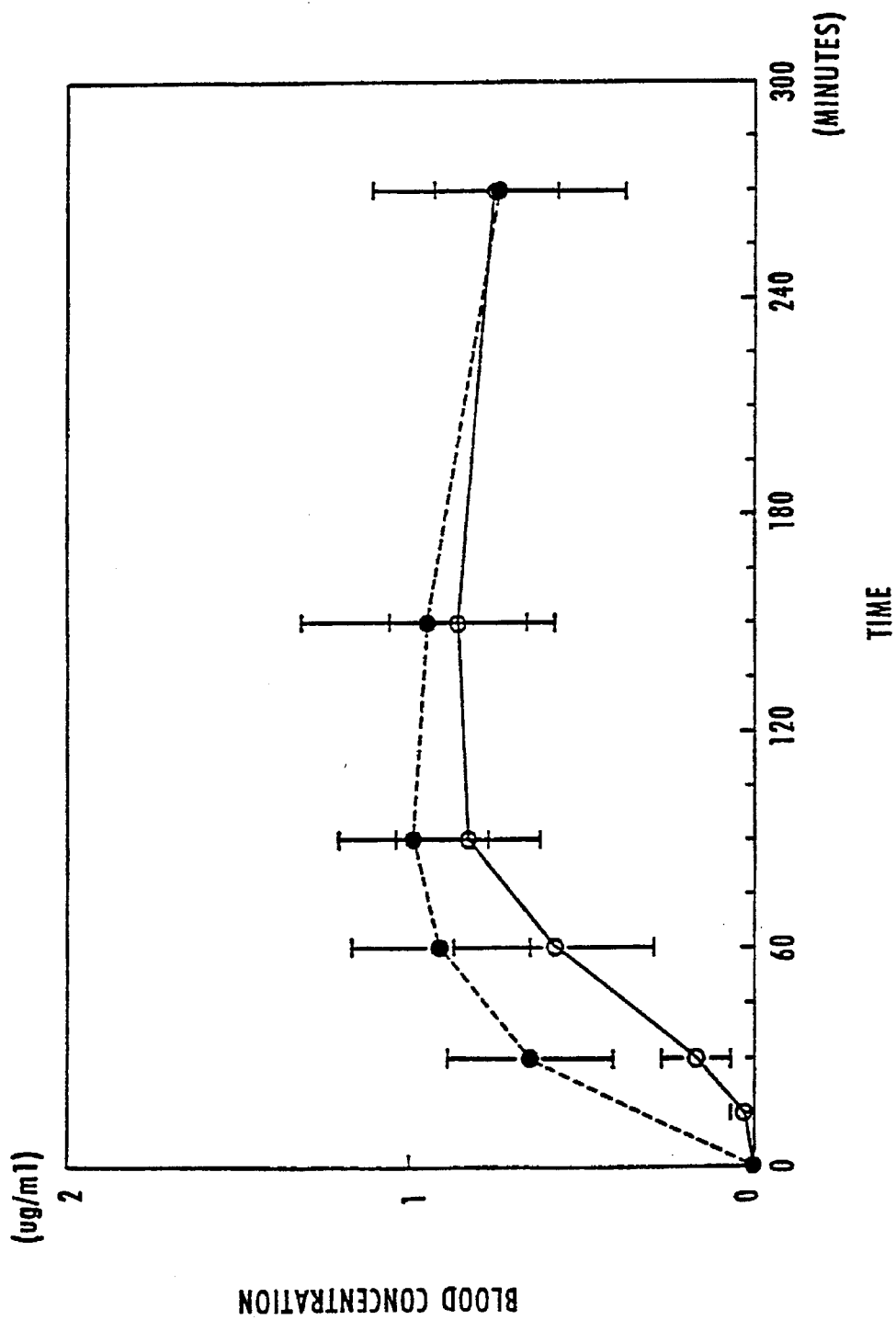
FIG. 3 is a graph showing the change in blood concentration over time after cyclosporin microemulsion concentrate containing dimethylisosorbide as a cosurfactant according to Example 7 (●—●) and cyclosporin emulsion concentrate containing ethanol as a cosurfactant (○—○) (SANDIMMUN®) are orally administered to rabbit.

The results are illustrated at FIGS. 1, 2 and 3 for Examples 1, 6 and 7, respectively. As can be seen from FIGS. 1, 2 and 3, since the soft capsule preparation according to the present invention shows substantially the same blood level as that of the ethanol-containing soft capsule preparation according to the prior art, it is apparent that dimethylisosorbide used in the present invention exhibits a superior effect as to the stability of soft capsule formulation without influencing the bioavailability of cyclosporin.

EXAMPLE 10

The bioavailability of the microemulsion using dimethylisosorbide as a cosurfactant according to the present invention was compared with the bioavailability of an ethanol-containing preparation according to the prior art to estimate the influence of dimethylisosorbide on the bioavailability of cyclosporin in human body. In this experiment, 16 healthy volunteeres aging 20 to 25 in average were involved and the soft capsules as prepared in Example 6 and the commercialized product SANDIMMUN® using ethanol as a cosurfactant were used as the test preparation and the control preparation, respectively. In this experiment, both of the test preparation and the control preparation were administered in an amount of 400 mg as cyclosporin per human body to examine the biological equivalency between two preparations. The test was conducted by dividing the 16 volunteeres into two groups as described in the following and then subjecting them to the cross experiment according to a Latin square cross over design. The interval between Period I and Period II was eight days.

| Subject | Period I | Period II |
|---|---|---|
| Group I | Control Preparation | Test Preparation |
| Group II | Test Preparation | Control Preparation |

Blood was taken from the subjects before and 0.5, 1, 1.5, 2, 3, 4, 6, 8, 10 and 24 hours after the administration of each preparation in an amount of 8 ml each time and analyzed by means of a cyclosporin monoclonal analysis kit using monoclonal antibody to determine the concentration of cyclosporin in the whole blood and plasma. To 150 µl of whole blood or plasma which was treated with heparin as an anticoagulant were added 50 µl of a solubilization reagent and 300 µl of a precipitation reagent for whole blood and then the mixture was agitated for 10 seconds to precipitate the protein and centrifuged with 9500xg for 5 minutes to obtain the supernatant which was then analyzed with TDX system.

Figure 4:
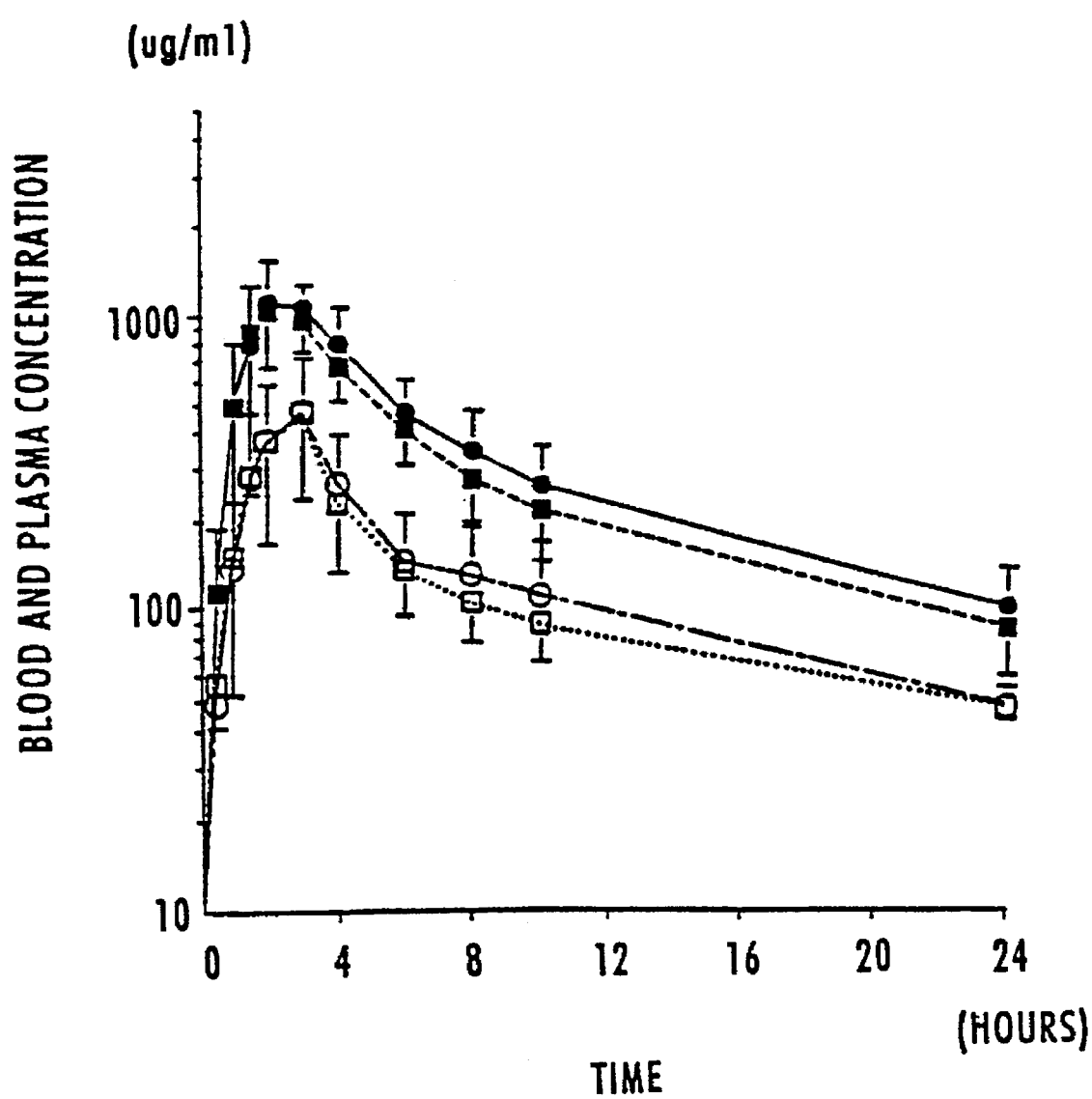
FIG. 4 is a graph showing the concentration of cyclosporin in the whole blood and plasma after the composition of Example 6 containing dimethylisosorbide as a cosurfactant according to the present invention and the commercialized product SANDIMMUN® are orally administered to human [●—● blood concentration of SANDIMMUN®; ■—■ blood concentration of the composition of Example 6 according to the present invention; ○—○ plasma concentration of SANDIMMUN®; □—□ plasma concentration of the composition of Example 6 according to the present invention].

The results are illustrated at FIG. 4. As can be seen from FIG. 4, since the soft capsule preparation according to the present invention shows substantially the same blood level as that of the ethanol-containing soft capsule preparation according to the prior art in human body, it is apparent that dimethylisosorbide used in the present invention has no effect on the bioavailability of cyclosporin.

Accordingly, the use of dimethylisosorbide as a cosurfactant in the cyclosporin-containing soft capsule according to the present invention effectively prolongs the shelf life of the capsules without adversely affecting bioavailability. Further, the cyclosporin pharmaceutical preparation according to the present invention overcomes a major problem in the soft capsules containing conventionally used cosurfactants, such as ethanol, propylene glycol, transcutol, glycofurol and the like. That is, the present invention alleviates membrane permeation of cosurfactant and the resulting change in the composition contained in the soft capsule which may lead to the crystallization of cyclosporin.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. An oral microemulsion composition for suppression of an immunological response comprising an immunosuppressive amount of cyclosporin and a sufficient amount of dimethylisosorbide, oil and surfactant to form a microemulsion suitable for oral administration, said cyclosporin, dimethylisosorbide, oil and surfactant being present in a ratio of 1:1-5:1-5:2-10, by weight.

2. The oral microemulsion composition of claim 1 further including a pharmaceutically acceptable adjuvant or excipient therefor.

3. The oral microemulsion composition of claim 1 wherein said cyclosporin is cyclosporin A.

4. The oral microemulsion composition of claim 1 wherein said oil is selected from the group consisting of: an animal oil having an iodine value of 180 to 200, a vegetable oil having a hydroxyl value of 150 or more, and a mixture thereof.

5. The oral microemulsion composition of claim 4 wherein said oil is refined fish oil.

6. The oral microemulsion composition of claim 1 wherein said oil further includes a saturated fatty acid.

7. The oral microemulsion composition of claim 1 wherein said oil is selected from the group consisting of: caprilic acid, capric triglyceride, and a mixture thereof.

8. The oral microemulsion composition of claim 1 wherein said surfactant is selected from the group consisting of: apricot kernel oil PEG-6 ester, the reaction products of castor oil and ethylene oxide, polyoxyethylene alcohols, sorbitan fatty acid esters and a mixture thereof.

9. The oral microemulsion composition of claim 1 wherein said cyclosporin, said dimethylisosorbide, said oil and said surfactant are present in a ratio of 1:2-4:2-5:2-7, by weight.

10. The oral microemulsion composition of claim 1 formulated into a soft gelatin capsule.

* * * * *